United States Patent
Troup et al.

(10) Patent No.: US 10,648,992 B2
(45) Date of Patent: May 12, 2020

(54) METHODS AND COMPOSITIONS RELATED TO LIPOPROTEINS IN BLOOD SAMPLES

(71) Applicant: SPECTRACELL LABORATORIES, INC., Houston, TX (US)

(72) Inventors: Jan M. Troup, Houston, TX (US);
Jane E. Lines, Houston, TX (US);
Christina P. Tan, Houston, TX (US);
Kristina Henkel Holan, Houston, TX (US)

(73) Assignee: SPECTRACELL LABORATORIES, INC., Houston, TX (US)

( * ) Notice: Subject to any disclaimer, the term of this patent is extended or adjusted under 35 U.S.C. 154(b) by 95 days.

(21) Appl. No.: 15/513,200

(22) PCT Filed: Sep. 25, 2015

(86) PCT No.: PCT/US2015/052359
§ 371 (c)(1),
(2) Date: Mar. 22, 2017

(87) PCT Pub. No.: WO2016/049528
PCT Pub. Date: Mar. 31, 2016

(65) Prior Publication Data
US 2017/0299617 A1    Oct. 19, 2017

Related U.S. Application Data

(60) Provisional application No. 62/056,312, filed on Sep. 26, 2014, provisional application No. 62/204,015, filed on Aug. 12, 2015.

(51) Int. Cl.
*G01N 33/92* (2006.01)

(52) U.S. Cl.
CPC ....... *G01N 33/92* (2013.01); *G01N 2333/775* (2013.01); *G01N 2440/00* (2013.01); *G01N 2800/32* (2013.01); *G01N 2800/50* (2013.01)

(58) Field of Classification Search
None
See application file for complete search history.

(56) References Cited

U.S. PATENT DOCUMENTS 7,856,323 B2    12/2010    Troup
2014/0178488 A1    6/2014    Minatelli et al.

OTHER PUBLICATIONS

Panzenboeck et al., "Effects of Reagent and Enzymatically Generated Hypochlorite on Physicochemical and Metabolic Properties of High Density Lipoproteins", The Journal of Biological Chemistry, vol. 272, No. 47, Issue 21, (1997), pp. 29711-29720.
Pourfarzam et al., "Association Between Myeloperoxidase and Free 3-Nitrotyrosine Levels in Patients with Coronary Artery Disease", International Journal of Clinical Medicine, vol. 4, (2013), pp. 158-164.
Zhang et al., "Association Between Myeloperoxidase Levels and Risk of Coronary Artery Disease", Journal of American Medical Association, vol. 286, No. 17, (2001), pp. 2136-2142.

*Primary Examiner* — Blaine Lankford
(74) *Attorney, Agent, or Firm* — Norton Rose Fulbright US LLP (57) ABSTRACT

Methods and compositions related to lipoproteins reactions are provided. Particularly, quantitation of lipoprotein subgroup particle numbers may be used to detect lipoprotein's response to oxidation conditions and incubation conditions. In further aspects, ultracentrifugation may be improved to analyze the lipoprotein profiles. Embodiments are directed to methods for generating a oxidation susceptibility measure for serum lipoproteins. In certain aspects a first portion of a serum sample is used to generate a base lipid particle profile (LPP) and a second portion of the serum sample is used to generate an oxidized lipid particle profile.

19 Claims, 1 Drawing Sheet

METHODS AND COMPOSITIONS RELATED TO LIPOPROTEINS IN BLOOD SAMPLES

CROSS-REFERENCE TO RELATED APPLICATIONS

This application is a national phase application under 35 U.S.C. § 371 of International Application No. PCT/US2015/052359, filed Sep. 25, 2015, which claims the benefit of U.S. Provisional Application No. 62/056,312, filed Sep. 26, 2014 and U.S. Provisional Application No. 62/204,015, filed Aug. 12, 2015. The contents of the referenced applications are incorporated into the present application by reference.

BACKGROUND OF THE INVENTION

1. Field of the Invention

The present invention relates generally to the field of clinical medicine. More particularly, it concerns the analysis and quantification of lipoproteins.

2. Description of Related Art

Lipoproteins have been identified as potential markers for cardiovascular disease risks. For example, the development of atherosclerosis is linked to a dysfunction in lipid metabolism. Cholesterol and triacylglycerol content and the distribution of cholesterol and triacylglycerol between high density lipoproteins and low density lipoproteins comprise parameters to determine a "cardiac risk profile" for coronary heart disease. Several classes of lipoproteins have been identified: very-low-density lipoproteins (VLDL), low-density lipoproteins (LDL), and high-density lipoproteins (HDL).

However, there still exists a need for rapid, accurate, and reproducible assays for the separation and identification, and quantitation of lipoproteins and their chemical properties.

SUMMARY OF THE INVENTION

Embodiments are directed to methods for generating a oxidation susceptibility measure for serum lipoproteins. In certain aspects a first portion of a serum sample is used to generate a base lipid particle profile (LPP) and a second portion of the serum sample is used to generate an oxidized lipid particle profile. The method can further comprise using a third portion of the serum sample to generate a non-oxidized lipid particle profile where the third portion of the serum sample has been incubated for a predetermined period of time at an elevated temperature without the addition of an external oxidizing agent. The differences between the base LPP and the oxidized LPP, or the base LPP and the non-oxidized LPP, or the oxidized LPP and non-oxidized LPP can be determined and analyzed. Alterations in the composition of the various subgroups of lipid particles can be used to generate data that can be used to diagnose, prognose, or classify individuals based on their LPP profiles or their oxidation susceptibility profiles. Each of the various subgroups of lipid particle may show an increase or decrease in particle number with various combinations of data being used to diagnose, prognose, or classify various diseases or conditions.

Methods and compositions may be provided for oxidizing lipids and/or lipoproteins in a test blood sample or portion thereof. In certain aspects, methods may comprise reacting a test blood sample or sample portion with at least one external oxidizing agent. The external oxidizing agent may be myeloperoxidase and hydrogen peroxide ($H_2O_2$), or their product, such as hypochlorite or hypochlorous acid, or any known oxidants in the art.

Certain embodiments are directed to methods for generating one or more lipoprotein profiles (LPP) for evaluating oxidation susceptibility in a test blood sample, comprising one or more of: (a) processing a test blood sample by (i) reacting a portion of the test blood sample with at least an externally added oxidizing agent; (ii) incubating a portion of the test blood sample at an elevated temperature for a predetermined time; or (iii) processing a portion of the test blood sample without reacting or incubating the test blood sample; (b) separating the processed portion of the test blood sample or fractionating the sample portion into VLDL (very low density lipoprotein), IDL (intermediate density lipoprotein), LDL I, LDL II, LDL III, LDL IV, HDL (high density lipoprotein) HDL 2b, HDL 2a and HDL 3 subgroups; and (c) measuring (i) a particle number increase or decrease, and/or (ii) cholesterol increase or decrease in one or more of the subgroups relative to a control or a reference level. In certain embodiments, the methods can further comprise calculating cholesterol ester transfer protein (CETP) activity based on the lipoprotein profile. In certain aspects the CETP activity can be increased or decreased relative to an un-oxidized control or reference level. In certain aspects the evaluation of the oxidation susceptibility is indicative of a healthy or unhealthy individual.

In certain aspects the test blood sample is a serum sample, a whole blood sample, or a plasma sample. In a further aspect the test blood sample is a serum sample.

The control or reference level can be an unoxidized control or a predetermined reference level. In certain aspects the unoxidized control can be a sample portion processed under the same reaction conditions with the exception of an externally added oxidant. A reference level can also include an unincubated control or reference level, that is a sample portion that was not exposed to an external oxidant or incubated at an elevated temperature. In certain aspects an elevated temperature is a temperature that is higher than the storage temperature. In certain aspects the portion of the sample used as a reference can be freshly prepared sample or a previously stored sample that has not been exposed to incubation or oxidization. In a further aspect the reference can be processed in parallel with other sample portions, that is incubated in a buffer for the same time and the same dilution ratio as the test blood sample exposed to incubation or oxidation. In certain aspects the unoxidized control is process directly from storage conditions or from a sample that has been freshly prepared.

The externally added oxidizing agent may have a concentration of about, at least about, or at most about 0.0001, 0.0002, 0.0005, 0.001, 0.002, 0.010, 0.050, 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0 µg/µl, µg/ml mg/µl or more (or any range derivable therein) or at least about, or at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 1000 ppm (or any range derivable therein). In particular embodiments, the externally added oxidizing agent may be 0.001 to 0.01 µg/µl myeloperoxidase and 0.1 to 1.0 mM $H_2O_2$. In further embodiments, the externally added oxidizing agent may be 50 to 150 ppm hypochlorite or hypochlorous acid.

The reaction conditions, such as oxidizing conditions or incubation conditions, may include a buffered medium, such as a Tris buffer or a phosphate buffer or other known physiologic buffer. The reaction conditions such as oxidizing conditions or incubation conditions may include a constant or variable temperature in the range of 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100° C. (or any range derivable therein), or more particularly 31, 32, 33, 34, 35, 36, 37, 38, 39, 40, 41, 42, 43, 44, or 45° C. (or any range derivable therein).

The reaction conditions such as oxidizing conditions or incubation conditions may include a period of at least, about, or at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 minutes, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 hour or any range derivable therein.

In certain aspects the test blood sample or portion thereof is separated or fractionated into one, two, three, four, five, six, seven or more of the following fractions or subgroups: VLDL (very low density lipoprotein) I, VLDL II, VLDL III, IDL (intermediate density lipoprotein), LDL I, LDL II, LDL III, LDL IV, HDL (high density lipoprotein) 2b, HDL 2a, and HDL 3 subgroups. In certain aspects the lipoprotein subgroups may be separated by any method known in the art, including, but not limited to, ion mobility, electrophoresis, nuclear magnetic resonance (NMR), or analytical ultracentrifugation. In certain aspects the separation is performed gradient centrifugation. The gradient may range in density from a starting point of 1,000, 1.0010, 1.0011, 1.0012, 1.0013, 1.0014, 1.0015, 1.0016, 1.0017, 1.0018, 1.0019, 1.0020 g/ml or any range derivable therein. On the other hand, the gradient may have an ending point of 1.2100, 1.2200, 1.2300, 1.2400, 1.2500, 1.2600, 1.2700, 1.2800, 1.2900, 1.3000, 1.3100, 1.3200, 1.3300, 1.3400, 1.3500, 1.3600, 1.3700, 1.3800, 1.3900, 1.400 g/ml or any range derivable therein. In a particular embodiment, the gradient may be from 1.000 to 1.300 g/ml. The gradient may be continuous or discontinuous. The gradient-forming agent may be Nycodez, iodixanol or a combination thereof or any agent known in the art. Nycodenz is 5-(N-2,3-dihydropropylacetamido)-2,4,6-triiodo-N,N'-bis(2,3-dihydropropyl) isophthalamide). Iodixanol is 5-5'-[2-hydroxy-1,3-propanediyl)-bis-(acetylamino)] bis [N,N'-bis(2,3-dihydroxypropyl-2,4,6,-triiodo-1,3-benzenecarboxamide].

In certain aspects the gradient is a continuous Nycodez gradient ranging in density from 1.000 g/ml to 1.300 g/ml by centrifuging at about 120,000 rpm at 22° C. for 1 hour. In certain aspects about 10-300 μL of layering solution are used. In a further aspect about 50-150 μL can be used. In still a further aspect about 60 μL can be used. After the storing step (within 1, 2, 3, 4, 5, 6, 7, 8, 10 minutes or hours), the contents of the centrifuge tube is extracted with a plunger device having a hole in a center of the plunger (a plunger device available from Brandel is suitable, although others may be used). Any other device, known to those of ordinary skill in the art, which would deliver the contents of the centrifuge tube without substantial mixing of the segregated components is also applicable. In a particular embodiment, the contents of the plunger may be delivered into a fluorescence detector except for the last amount which is pushed out of the transfer tubing with an HPLC pump.

In certain embodiments, the blood sample may be incubated or reacted at a temperature and for a time sufficient to facilitate uptake of a dye/label or other analyte. In certain aspects a fluorescent agent (e.g., a NBD fluorophore) can be added to the test sample before or during the separation process. The fluorescent agent can be detected. A detector can be used to monitor and detect the various fractions and producing a profile for the processed sample. The detector can be calibrated and, in the case of use of a fluorophore as the analyte, its setting adjusted to the emission and/or absorbance wavelengths of the dye/label to be monitored or detected. In certain aspects a flow technique can be used. Such methods may further include correcting the resulting profile data for start position and first signal.

Additional aspects involve measuring particle number (percentage or amount), or cholesterol increase or decrease in the IDL, LDL I, LDL II, LDL III, LDL IV and HDL 2b, HDL 2a, and HDL 3 subgroups relative to a control or a reference level. These measurements can be used to generate a lipoprotein profile.

Measuring relative to a control or a reference level can include one or more of: (i) measuring a particle number increase or cholesterol decrease in the LDL I subgroup; (ii) a particle number decrease or cholesterol decrease in the LDL II subgroup; (iii) a particle number decrease or increase or cholesterol increase or decrease in the LDL III subgroup; (iv) a particle number decrease or cholesterol increase in the VLDL subgroups; (v) a particle number increase or cholesterol increase in the HDL2b group; (vi) a particle number decrease or increase or cholesterol decrease or increase in the HDL 2a subgroup; and/or (vii) a particle number decrease or cholesterol decrease in the HDL3 subgroup. The various measures can be used to identify a healthy or unhealthy lipoprotein profile.

In further embodiments, the methods may comprise calculating a decrease of the CETP activity, relative to an un-incubated control, based on one or more of (i) a particle number minor change or cholesterol minor change in the LDL I subgroup; (ii) a particle number minor change or cholesterol minor change in the LDL II subgroup; (iii) a particle number minor change or cholesterol minor change in the VLDL subgroups; (iv) a particle number increase or cholesterol increase in the HDL2b group; and/or (v) a particle number decrease or cholesterol decrease in the HDL3 subgroup, therefore revealing a healthy lipoprotein profile.

In other embodiments, the methods may comprise calculating an increase of the CETP activity, relative to an un-incubated control, based on one or more of (i) a particle number increase or cholesterol decrease in the LDL I subgroup; (ii) a particle number decrease or cholesterol decrease in the LDL II subgroup; (iii) a particle number decrease or cholesterol increase in the VLDL subgroups; (iv) a particle number increase or cholesterol decrease in the HDL2b group; and/or (v) a particle number decrease or cholesterol increase or decrease in the HDL3 subgroup, therefore revealing an unhealthy lipoprotein profile.

In certain embodiments, the measuring step, particularly in the incubation methods, comprises measuring a particle number (percentage or amount) increase/decrease or cholesterol increase/decrease in the LDL I subgroup and/or LDL II subgroup, and/or a particle number (percentage or amount) increase/decrease or cholesterol increase/decrease in VLDL subgroups, such as VLDL-L and/or VLDL-S.

In certain aspects measuring can include determining the particle number (percentage or amount) decrease in the VLDL subgroup and cholesterol increase in the VLDL subgroup, thereby determining the activation of VLDL-CETP and/or generating an unhealthy lipoprotein profile. In other aspects, the step may comprise measuring the particle number (percentage or amount) increase in the VLDL subgroup and cholesterol decrease in the VLDL subgroup, thereby determining the deactivation of VLDL-CETP and/or revealing a healthy lipoprotein profile.

In a further aspect measuring can include determining the particle number (percentage or amount) decrease in the VLDL subgroup and cholesterol increase in the VLDL subgroup, thereby determining the activation of VLDL-CETP and/or revealing an unhealthy lipoprotein profile.

In other embodiments, the measuring step comprises measuring a particle number (percentage or amount) increase or cholesterol increase in the HDL2b group and a particle number (percentage or amount) decrease or cholesterol decrease in one or more of the HDL3 subgroups and/or further comprises calculating the activity of lecithin cholesterol acyltransferase (LCAT) in the test blood sample, thereby generating a lipoprotein profile.

In further embodiments, the measuring step comprises measuring a particle number (percentage or amount) increase or cholesterol increase in the HDL2b group and a particle number (percentage or amount) decrease or cholesterol decrease in one or more of the HDL3 subgroups and/or further comprises calculating the activity of lecithin cholesterol acyltransferase (LCAT) in the test blood sample, thereby generating a lipoprotein profile.

Certain embodiments are directed to diagnosing a subject for risk of having or developing a disease or condition based on the LPP(s). In certain aspects the subject is identified as having a risk of developing cardiovascular diseases, such as atherosclerosis. In some embodiments, the method further comprises monitoring or treating a subject based on the diagnosis or the lipoprotein profile.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

In certain aspects, a personalized lipoprotein profile may be generated by lipoprotein analysis in a subject. In further aspects, the lipoprotein profile may be generated in oxidization assays or incubation assays as described in following sections.

The lipoprotein profile, including a healthy profile and/or an unhealthy profile, may be used to diagnose, predict, monitor the health of a subject, especially cardiovascular health. In additional aspects, the lipoprotein profile may be used in prescribing, recommending or administrating treatment methods for improving health and for monitoring the efficacy/response of particular treatment methods, including any health improvement methods. For example, the health improvement methods may include administering, prescribing, or recommending antioxidants, or reduce oxidants, such as quit smoking, reducing exercise, or reducing drinking of chlorinated water.

I. LIPOPROTEINS

In certain aspects, lipoproteins may be analyzed to generate a personalized lipoprotein profile used in health assessment and/or improvement.

A lipoprotein is a biochemical assembly that contains both proteins and lipids, bound to the proteins, which allow fats to move through the water inside and outside cells. The proteins serve to emulsify the lipid molecules. Many enzymes, transporters, structural proteins, antigens, adhesins, and toxins are lipoproteins. Examples include the plasma lipoprotein particles classified under high-density (HDL) and low-density (LDL) lipoproteins, which enable fats to be carried in the blood stream, the transmembrane proteins of the mitochondrion and the chloroplast, and bacterial lipoproteins Cholesterol and triacylglycerols are transported in the blood by lipid-containing particles known as lipoproteins. The most important of these lipoproteins are high density lipoprotein (HDL), low density lipoprotein (LDL), very low density lipoprotein (VLDL). Of these components, HDL cholesterol can be measured directly by precipitating all apoB-containing lipoproteins (VLDL and LDL). VLDL contains most of the triacylglycerol. There are usually five grams of triacylglycerols for every gram of cholesterol in VLDL. LDL has traditionally been estimated by subtraction of HDL and VLDL cholesterol from total cholesterol.

Lipoproteins may be classified as follows, listed from larger and less dense to smaller and denser. Lipoproteins are larger and less dense when the fat to protein ratio is increased. They are classified on the basis of electrophoresis and ultracentrifugation.

Chylomicrons carry triacylglycerols (fat) from the intestines to the liver, to skeletal muscle, and to adipose tissue.

Very-low-density lipoproteins (VLDL) carry (newly synthesised) triacylglycerols from the liver to adipose tissue.

Intermediate-density lipoproteins (IDL) are intermediate between VLDL and LDL.

Low-density lipoproteins (LDL) carry 3,000 to 6,000 fat molecules (phospholipids, cholesterol, triacylglycerols, etc.) around the body. LDL particles are sometimes referred to as "bad" lipoprotein because concentrations, dose related, correlate with atherosclerosis progression, including large buoyant LDL (lb LDL) particles and small dense LDL (sd LDL) particles. Lipoprotein(a) is an LDL with apo-lipoprotein (a).

High-density lipoproteins (HDL) collect fat molecules (phospholipids, cholesterol, triacylglycerols, etc.) from the body's cells/tissues, and take it back to the liver. HDLs are sometimes referred to as "good" lipoprotein because higher concentrations correlate with low rates of atherosclerosis progression and/or regression.

Certain embodiments determine the particle number of lipoprotein subgroups. Particle size is highly correlated to density with small corresponding to dense particles and large corresponding to buoyant particles. The main groups of lipoproteins include VLDL, LDL and HDL. Subgroups of LDL include IDL (intermediate density lipoprotein), LDL I, LDL II, LDL III, and LDL IV. HDL subgroups include HDL 2b, HDL 2a, and HDL 3 subgroups. Other subgroups according to density, currently defined or undefined, may be quantified with certain embodiments of the present method as well.

As used herein, "buoyant" in reference to lipoproteins means lipoprotein particles that are predominately larger or more buoyant that the average population. "Predominantly buoyant" with respect to lipoprotein samples means mean density value less than 1.032 $g/cm^2$ for LDL and less than 1.100 $g/cm^2$ for HDL.

As used herein, "dense" in reference to lipoproteins means lipoprotein particles that are predominately smaller or more dense that the average population. "Predominantly dense" means with respect to lipoprotein samples means mean density value greater than 1.032 $g/cm^2$ for LDL and greater than 1.100 $g/cm^2$ for HDL.

II. OXIDATION OF LIPOPROTEINS

Certain aspects involve the development of an assay to quantify the oxidative susceptibility (response) of LDL for an individual. Such quantification may be used to generate a lipoprotein profile for health assessment and/or improvement.

The "LDL Oxidative Response" result is a measure of new dense particles being generated as a result of oxidation by an oxidizing agent such as externally added hypochlorous acid (100 ppm). For example, the more dense particles are the result of adding chlorine to unsaturated lipids making them more dense. This could be measured as a percent change over the same sample incubated under the same conditions without the oxidizing agent. In certain aspects, the result is a measure of a person's defense system to LDL oxidation but could also be related to the defense against other tissue oxidation and/or aging.

"LDL Oxidative Response" may be more than a measure of the production of oxidized LDL particles over the incubated control. One would think the incubated sample is a true control for the oxidation assay since the two processes are identical except that hypochlorous acid for the oxidation is added. However, in the production of oxidized LDL particles it appears that some of the peak movement due to CETP activity was prevented, since the resulting profile is often very similar to the unchanged LPP profile. This has the effect of magnifying the amount of apparent oxidized LDL produced. This happens when one would expect an unhealthy profile from high triacylglycerols. The oxidizing assay may also denature some of the CETP with the oxidizing agent so the control is also affected by the assay.

Both the oxidation of LDL and the denaturing of CETP activity on LDL can be considered "LDL Oxidative Response." Both are related to an atherogenic process and the formation of plaque. The oxidation process is associated with cellular aging as well as LDL oxidation. High triacylglycerols, when often associated with diabetes, is an oxidative process causing atherosclerosis, plaque formation and aging.

It may be that the denaturing of CETP is more of an important step than the current understanding that CETP activity is atherogenic since it leads to small-dense LDL and low HDL, which are atherogenic. There may be benefits of CETP that outweigh the obvious disadvantages. In fact new drugs like torcetrapib and dalcetrapib, that inhibit CETP, were found to give poor outcomes.

In any event, all of the processes from the oxidation experiment can be called "LDL Oxidative Response," which may include LDL oxidation and/or inhibition of CETP activity.

The oxidation of low density lipoprotein (LDL) is a key step in the formation of foam cells that build atherosclerotic lesion and plaque. Macrophage cells in the arterial intima target oxidized LDL (Ox-LDL) and become engorged with lipids forming fatty deposits known as foam cells which accumulate to form in atherosclerotic lesions. These lesions are not observed in normal healthy arteries. Medium to small size LDL must be oxidized to be targeted by macrophage receptors however the largest subgroup of LDL known as IDL plus the smallest subgroup of VLDL together known as remnant like particles or remnant lipoprotein (RLP) is taken up by macrophages even without going through the oxidation step, making these particles particularly atherogenic. However, if RLP is oxidized it is even more readily taken up by macrophage cells than the smaller oxidized LDL particles.

LDL oxidation affects both the lipid and protein components of LDL and this process may begin with the oxidization of circulating LDL. The oxidation of LDL is not simply one chemical process but rather the generation of a variety of oxidization products from the lipoprotein particle. It appears that even if the particle has minimally oxidized lipid components it can become the target of macrophage cells and can lead to atherosclerotic lesions. Partially oxidized LDL can involve lipid peroxidation or the formation of chlorohydrin and as the process proceeds, the chemical oxidation of Apo B-100 protein side chains occurs. Lipid peroxidation is a free radical chain reaction attack on the unsaturated fatty acids of the lipoproteins to form shorter chain aldehydes and other species. These smaller molecules are then lost by the lipoprotein particle and result in an increase of the LDL and HDL particle densities from the proportional decrease in lipid content and an increase in the proportional heavier protein content of the particle. This oxidation produces 4-hydroxynonenal and malondialdehyde products which are capable of attaching to the lysine residues of Apo B-100 as confirmed by immunological analysis.

Another lipoprotein oxidization process can take place by the action of hypochlorous acid from myeloperoxidase on unsaturated fatty acids to form chlorohydrins. This process appears to be favored over lipid peroxidation when compared in oxidization experiments. In the chlorohydrin formation there is an addition of a chlorine atom on one side of the double bonds and a hydroxyl on the other side causing an increase the overall weight and density of the lipoproteins as shown by mass spectrometry.

Although the process of atherogensis has been well studied many questions still remain regarding the presence of Ox-LDL in circulating blood and the possibility that Ox-LDL may be transferred between lesions and the circulation. In isotope studies Ox-LDL was shown in rats to be cleared by the liver in minutes leaving remarkably low levels of circulating Ox-LDL. However, patients with coronary artery disease were found to have elevated blood serum levels of Ox-LDL and it was associated with both subclinical and clinical atherosclerosis leaving researcher to conclude that the measurement of serum Ox-LDL is a good indicator of developing atherosclerosis.

Current available Ox-LDL assays target murine monoclonal antibody, mAb-4E6 or malondialdehyde (MDA) as specific oxidization products and these methods have shown good correlation with known atherosclerotic disease however it is not clear that all or even most LDL oxidation processes proceed by these routes. In fact there is good evidence that LDL is oxidized by myeloperoxidase-generated hypochlorous.

The human body protection against LDL oxidation may consist in part to the level of accumulated anti-oxidants which are present in the blood stream and tissues such as the arterial intima. The level of antioxidant and the protection being provided is hard to measure but the oxidative susceptibility (response) of LDL can be measured in vitro. Many different approaches have been tested for LDL oxidation, so a reasonable oxidation method was searched for that had a basis as close as possible to natural oxidative processes in humans.

The oxidizing agent that may be used include $H_2O_2$, myeloperoxidase (MPO) and finally hypochlorous acid (HOCl). Thus, oxidizing LDL with MPO, and $H_2O_2$ to duplicate a possible natural oxidative process may be performed in some particular embodiments. Additionally, since the most likely end product from MPO is the production of HOCl, this agent may be an option of an oxidizing agent. HOCl is also a common additive in most of the world's water supply so it was intriguing to see what levels of this agent were needed for significant LDL oxidation.

III. INCUBATION ASSAYS

Certain aspects involve the use of incubation assays to generate a lipoprotein profile for health assessment and/or improvement.

In the development of the oxidized LDL assay it was discovered that the control profile also changed relative to a standard LPP particle number profile. This change gives additional information on an individual's lipoprotein enzyme activity that has been activated by incubation. Thus, certain embodiments provide additional assays that have resulted from this observation and these results may give important insight into atherogenesis for an individual.

The two most important enzymes that play a role in lipoprotein metabolism and are the likely activated in the incubation experiment are cholesterol ester transfer protein (CETP) and lecithin cholesterol acyltransfererase (LCAT).

CETP is important in the transfer of triacylglycerols from VLDL particle to LDL and HDL and the reverse transfer of cholesterol ester from LDL and HDL back to VLDL particles. This movement of lipids occurs when triacylglycerols are elevated and the activity of CETP is high and is the pivotal event in the formation of cholesterol depleted or triacylglycerol enriched LDL and HDL and the formation of small-dense LDL and small HDL. In the case of HDL this leads to the loss of Apo A1 which is renally eliminated and the consequentially reduction of HDL in these patients. The constellation of lipid levels, namely elevated triacylglycerols, small-dense LDL and low HDL are the main components of Metabolic Syndrome which has been shown to increase cardiovascular risk and lead to insulin resistance.

The components of Metabolic Syndrome each contribute to atherosclerosis. Elevated triacylglycerols can further lead to the production of VLDL remnants which are very atherogenic particles that don't need to be oxidized to be taken up by macrophage cell to form plaque. Small-dense LDL penetrates the endothelial lining of the arteries more rapidly than large LDL particles, is more easily oxidized and is less recognized by LDL receptors than large LDL allowing these particles to stay in circulation longer and making them very atherogenic as well. HDL's main function is to remove excess cholesterol from cells and return it to the liver. When levels of HDL are low studies have shown this to lead to increase plaque formation and cardiovascular events. CETP activity is important in all of these processes and understanding its activity can shed light on the vulnerability of a patient to atherosclerosis.

HDL metabolism commonly referred to as reverse cholesterol transport is an important process by which small HDL3 particles enter cells and gather up un-esterified cholesterol, which is then esterifed by the enzyme LCAT to form cholesterol ester. When the HDL particle is loaded with cholesterol ester, it becomes HDL2b, and these particles return to the liver to drop off their cholesterol stores. The LCAT activity is important in this process and the removal of excess cholesterol, so the measure of its activity is important in reverse cholesterol transport and the health of an individual.

IV. SAMPLES

Samples can be prepared, stored, or transported for the use in certain embodiments. The sample can be a whole blood sample, a serum sample or a plasma sample.

A. Sample Collection

Samples such as a blood sample may be procured. This can be done any way known to those of ordinary skill in the art, including collecting a blood sample via a venous draw into red top tubes with no anticoagulant or via a finger stick technology using an EDTA or other suitable anticoagulant.

Said sample can be obtained by conventional methods by using methods well known to those of ordinary skill in the related medical arts by a medical professional. In some embodiments the biological sample may be obtained by a physician, nurse, or other medical professional such as a medical technician or phlebotomist or from the test subject himself or herself. The medical professional may indicate the appropriate test or assay to perform on the sample.

B. Sample Storage

In certain aspects, a sample may be obtained and prior to analysis by one or more methods described herein, the sample may be stored for a length of time. A length of time may include a time interval such as seconds, minutes, hours, days, weeks, months, years or longer. In some cases, the sample obtained from a subject is subdivided prior to the step of storage or further analysis.

The storage temperature may be explicitly defined or defined by a temperature range. The sample may be stored at room temperature or at reduced temperatures such as cold temperatures (e.g. between about 20° C. and about 0° C.), or freezing temperatures, including for example 0° C., −1° C., −2° C., −3° C., −4° C., −5° C., −6° C., −7° C., −8° C., −9° C., −10° C., −12° C., −14° C., −15° C., −16° C., −20° C., −22° C., −25° C., −28° C., −30° C., −35° C., −40° C., −45° C., −50° C., −60° C., −70° C., −80° C., −100° C., −120° C., −140° C., −180° C., −190° C., −200° C. or any ranges or values derivable therein. The sample may be stored in any condition or environment that allows or achieves the desired temperature condition. In some cases, the samples may be stored in a refrigerator, on ice or a frozen gel pack, in a freezer, in a cryogenic freezer, on dry ice, in liquid nitrogen, or in a vapor phase equilibrated with liquid nitrogen.

The sample container may be any container suitable for storage and or transport of the biological sample including but not limited to: a cup, a cup with a lid, a tube, a sterile tube, a vacuum tube, a syringe, a bottle, a finger stick capillary or any other suitable container. The container may or may not be sterile.

V. OXIDIZING AGENTS

In certain embodiments, oxidizing agents such as myeloperoxidase (MPO) and hydrogen peroxide ($H_2O_2$) and chloride anion ($Cl^-$) or hypochlorous acid (HOCl) may be used.

Myeloperoxidase (MPO) is a peroxidase enzyme that in humans is encoded by the MPO gene. Myeloperoxidase is most abundantly expressed in neutrophil granulocytes (a subtype of white blood cells). It is a lysosomal protein stored in azurophilic granules of the neutrophil. MPO has a heme pigment, which causes its green color in secretions rich in neutrophils, such as pus and some forms of mucus. MPO produces hypochlorous acid (HOCl) from hydrogen peroxide ($H_2O_2$) and chloride anion ($Cl^-$) (or the equivalent from a non-chlorine halide) during the neutrophil's respiratory burst. It requires heme as a cofactor. Furthermore, it oxidizes tyrosine to tyrosyl radical using hydrogen peroxide as an oxidizing agent. Hypochlorous acid and tyrosyl radical are cytotoxic, so they are used by the neutrophil to kill bacteria and other pathogens.

Hypochlorous acid is a weak acid with the chemical formula HClO. It forms when chlorine or hypochlorite dissolves in water, and it is HClO that actually does the disinfection when chlorine is used to disinfect water for human use.

VI. SEPARATION AND DETECTION METHODS

In certain embodiments, serum may be separated from a blood sample. In further embodiments, the serum may be mixed with a dye such as a fluorescent dye (although another analyte material may be used) and a self-generating gradient material to form an analyzable mixture. A serum sample, for example, between 1 and 100 µL, is used. More particularly, the volume of the serum sample is in the range of 1-30 µL, including, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 µL or any range or number derivable therein, most particularly, about 3 µL may be used.

The density gradient forming agent can be any agent that forms a density gradient when exposed to a centrifuge force field. Examples of such an agent include sucrose.

The dye can generally be any dye. For example, the dye is a visible or fluorescent dye. Examples of such dyes include NBD C6-ceramide (6-[N-(7-nitrobenz-2-oxa-1,3-diazole-4-yl) amino]hexanoyl-D-erythro-sphingosine; Molecular Probes, Eugene, Oreg., Cat. No. N-1154) and Sudan Black B. In some embodiments, the dye can be a lipophilic or protein stain. Examples of a lipophilic and protein stain include Sudan Black B and Coomassie Brilliant Blue R. The dye can also be a fluorescent membrane probe. Examples of such probes include NBD, DiI (3,3'-dioctadecylindocarbocyanine) (D-282), DiA (N,N-dipentadecylaminostyrilpyridinium), (D-3883), BODIPY (dipyrromethenboron difluoride) C5-HPC (D-3795).

The density gradient can be subject to ultracentrifuge for separation. The centrifuge force field can generally be any strength sufficient to separate the lipoprotein fractions. Particularly, the force field is at least about 400,000×g. A range of the force field strength is about 400,000×g to about 800,000×g. Specific examples of force field strength include about 400,000×g, about 450,000×g, about 500,000×g, about 550,000×g, about 600,000×g, 800,000×g, and ranges between any two of these values.

The multiple lipoprotein fractions can generally comprise any lipoprotein fractions. Example fractions include a VLDL fraction, a IDL fraction, a LDL fraction, a Lp(a) fraction, and a HDL fraction. A separated mixture may contain one or more of these fractions, depending on the composition of the original sample.

The visualizing step can comprise photographing the separated mixture. The photograph can be digitized into a computer and analyzed. Alternatively, the separated mixture can be scanned directly into a computer. A lipoprotein profile may be quantized to afford the concentration of the individual lipoprotein fractions.

The separated mixture may or may not be frozen and sliced to isolate the multiple lipoprotein fractions.

Isolated lipoprotein fractions can subsequently be analyzed by a variety of methods. These methods include capillary electrophoresis, solid phase extraction, mass spectrometry, thin layer chromatography, electron paramagnetic resonance, immobilized pH gradient isoelectric focusing, matrix assisted laser desorption/ionization (MALDI) mass spectrometry, electrospray ionization mass spectrometry (ESI-MS), and two dimensional gel electrophoresis.

A combination of capillary electrophoresis and electrospray ionization mass spectrometry may be used to prepare a lipoprotein profile or a lipoprotein oxidization profile and cardiac risk profile analysis (Macfarlane, R. D. et al., Electrophoresis 18: 1796-1806, 1997).

Ultracentrifugation and image analysis may be used to separate the VLDL, LDL, and HDL fractions. Each of the individual fractions may be further analyzed using capillary electrophoresis or other methods. Mass spectrometry may be used to determine the isoform distribution for apoproteins. Abnormalities in the lipid profiles may be observed with samples from every cardiac patient. The analyses may also be used to monitor the effects of a drug on a cardiac patient.

VII. CLINICAL APPLICATION

A number of clinical implication can be suggested by various increases or decrease with each individual measurement described herein. Examples of clinical application of the data produced using the methods described herein include. (i) If particles are decreased and triacylglycerols are elevated, reduce triacylglycerols through diet, exercise or therapy such as omega-3's, fibrates, statins or niacin. (ii) If particles are increased, reduce triacylglycerols and LDL through diet, exercise or therapy such as omega-3's, fibrates, statins or niacin. (iii) If particles are increased or moderately decreased, improve HDL functionality through exercise. (iv) If particles are increased and triacylglycerols are elevated, reduce triacylglycerols through diet, exercise or therapy such as omega-3's, fibrates, statins or niacin. (v) If particles are decreased, improve HDL functionality through exercise. (vi) If particles are increased, reduce oxidants (i.e. smoking, air pollution, chlorinated water) and increase anti-oxidants (i.e. fruits, vegetables, vitamins C & E, Co Q-10, N-acetyl cysteine, alpha lipoic acid).

A variety of possible disease states can be identified using the methods described herein. For example: (i) If triacylglycerols are elevated, metabolic syndrome, insulin resistance, diabetes, pancreatitis and atherosclerosis. (ii) Metabolic syndrome, insulin resistance, diabetes, pancreatitis and atherosclerosis. (iii) Poor lipid clearance and atherosclerosis. (vi) Atherosclerosis and accelerated aging. (vii) Atherosclerosis and accelerated aging.

VIII. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Human Serum Oxidation and Incubation Assay

Materials—30% Hydrogen peroxide ($H_2O_2$) and 2,2'-azobis-(2-amidinopropane) dihydrochloride (AAPH) was purchased from Sigma Aldrich (St. Louis, Mo.); Myeloperoxidase (MPO) and PBS were purchased from EMD Millipore (Darmstadt, Germany); Nycodenz was from Axis Shield; N-(7-nitrobenz-2-oxa-1,3-diazol-7-yl)-6-ceramide (NBD) from Molecular Probes was dissolved in dimethyl sulfoxide (DMSO) from Thermo Fisher Scientific (Waltham, Mass.); 5% Sodium hypochlorite was purchased from Thermo Fisher Scientific (Waltham, Mass.).

Serum collection—Serum is collected from fasting blood donors in serum separator tubes containing a coagulant accelerator, allowed to clot and separated by centrifugation at 3000 rpm for 10 minutes. Serum samples are stored at 4° C. for no more than 3 days.

Oxidation of LDL by AAPH—Serum was mixed with 750 mM AAPH for a final concentration of 24 mM APPH and incubated at 37° C. for 15 hours. Unoxidized control serum was also incubated.

Oxidation of LDL by HOCl—Serum was mixed with sodium hypochlorite (HOCl) and PBS for a final concentration between 1-300 ppm HOCl and incubated at 37° C. for 20 hours. Unoxidized control serum was mixed 1:1 with PBS and incubated as well. Solutions were diluted daily from a stock solution. 100 ppm was optimal.

The LDL oxidation method has detected a few percent of human serum LDL oxidation from hypochlorous acid (HOCl) treatment as low as 2 ppm when incubated at 37 degree C. or body temperature. Most of the world's water supplies have between 0.5 to 4.0 ppm free chlorine disinfectant, often from HOCl as in our LDL oxidation assay. It brings into question how safe is the water supply. This is especially concerning since human chlorinated water exposure, in relatively large quantities, is continuous every day activity.

LDL oxidation is an important step in the formation of foam cells and plaque leading to atherosclerosis. The wide spread use of water chlorination in the US began in the 1920's and 1930's and data shows cardiovascular disease doubling over this period by the 1950's. Water chlorination and cardiovascular disease increase may not be a coincidence.

Oxidation of LDL by MPO and $H_2O_2$—Serum was oxidized with myeloperoxidase (MPO) and hydrogen peroxide/$Cl^-$ (which need not be added) as well as with hydrogen peroxide ($H_2O_2$) alone. Serum was mixed with PBS and varying concentrations of $H_2O_2$. Serum was mixed with PBS and a final concentration of 0.002 ug/uL MPO and incubated at 37° C. for 30 minutes. Oxidation was initiated by the addition of 0.5 mM $H_2O_2$ and incubated at 37° C. for 20 hours.

ELISA—The oxLDL was measured using a capture or sandwich enzyme linked immunosorbent assay (ELISA) (Mercodia, Uppsala, Sweden) that is based on the maurine monclonal antibody 4E6.

Separation of lipoprotein particles by ultracentrifugation called the Lipoprotein Particle Profile—LPP. The LPP method was published as a patent, U.S. Pat. No. 7,856,323 dated Dec. 21, 2010 by Jan M. Troup, and assigned to Spectracell Laboratories, Inc. (incorporated herein by reference in its entirety).

LDL Oxidative Response Assay—Although the data processing and calculations of lipoprotein particle numbers remain the same as described in the patent the creation of the gradient for lipoprotein separation and the measurement of fluorescence have been modified. In 2012 the centrifuge tube preparation was modified to be robotically performed using an epMotion 5075 system (Eppendorf, N.Y.). Blood serum is premixed with a Nycodenz gradient from Thermo Fisher Scientific (Waltham, Mass.), and stained with NBD C6 Ceramide dye (catalog # N1154, Molecular Probes, Inc.) at a concentration of 1 mg/300 uL DMSO from Thermo Fisher Scientific (Waltham, Mass.). This solution is incubated at 22° C. for 30 minutes. A multilayer gradient is built robotically by pipetting the layers into centrifuge tubes which are then spun using a Discovery M120 SE and S120-AT3 rotor from Thermo Fisher Scientific (Waltham, Mass.) at 22° C. for 1 hour at 120 k rpm. This method produces a continuous gradient that ranges in density from 1.000 g/ml to 1.300 g/ml.

In 2013 the sample fluorescence measurement was changed to a modified version of a photographic readout system. After centrifugation the centrifuge tubes are layered with 60 ul of heptane from Thermo Fisher Scientific (Waltham, Mass.) to flatten the meniscus for measurement. The tube contents are then measured using a custom built fluorescence system (ThorLabs, Inc.) composed of a 1080 CCD camera, LED light source at wavelength 470 nm and a 515 nm emission filter. The resulting data is processed as previously described using Origin 8.6 Pro software (OriginLab Corporation) and is pasted into spreadsheet for report generation.

One goal was to develop a reproducible assay, using the patented LPP—lipoprotein particle profiling technology (U.S. Pat. No. 7,856,323, incorporated herein by reference in its entirety), to quantify the oxidative susceptibility (response) of LDL for an individual. In the development of the oxidized LDL assay it was observed that the assay control profile, which is serum incubated under the same conditions as in the oxidation experiment but un-oxidized, also changed relative to a standard LPP particle number profile. Although this change in the control profile is part of the oxidized LDL assay and an important step in the process, the change also gives additional information on an individual's lipoprotein enzyme activity that has been activated by incubation.

A number of additional assays have resulted from this observation and these give important insight into atherogenesis for an individual. Specifically, incubation of human serum creates a lipid transfer, mostly triacylglycerols, from VLDL to LDL, and is believed to be due to CETP activity and results in a decrease in the density of LDL lipoproteins. It may be contemplated that the measurement of the density change in the LDL lipoprotein profile can be used to quantify the result of CEPT activity. This density change was previously observed in incubated human serum but the measurement and underlining cause was not fully described. Additionally a similar, previously observed density change occurs and can be measured in the HDL lipoprotein profile and it is believed to be due to LCAT activation. These measurements together provide valuable insight into the lipoprotein metabolism of the individual.

The assay to access the susceptibility (response) of LDL to oxidation was developed using the ultracentrifugation lipoprotein separation and measurement methods described herein and using a controlled oxidation protocol. LDL was oxidized using the oxidizing agent hypochlorous acid. A control profile was used that had the same dilution conditions and incubation time as the oxidized sample. The resulting lipoprotein profile shows a particle number percentage increase in the heavier LDL II, III, IV and HDL 2b subgroups relative to the control profile which is believed to be due to the formation of chlorohydrins from the hypochlorous acid oxidation. The observation of the formation of the more dense LDL subgroups even going into the HDL density region indicates that hypochlorous acid is useful for an LDL oxidative susceptibility test. Furthermore the formation of dense particles and therefore the level of oxidation varied from sample to sample as would be expected from a random selection of serum specimens with varying levels of anti-oxidant protection. Additional experiments using myeloperoxidase to catalyze the combination of hydrogen peroxide and chloride ions to produce the oxidizing agent hypochlorous acid gave results similar hypochlorous acid.

The percent of oxidized lipids named "LDL Oxidative Response", of presumably mostly LDL particles, over a control sample was plotted against a number of other lipid and cardiovascular markers. The highest positive correlations were found with triacylglycerols, LDL III and Apo B-100. A high positive correlation was also seen in the LDL Oxidative Response marker to an in-house survey from volunteer donors where the consumption of food and supplement antioxidants was low and/or when the volunteers had oxidative stress from smoking or cancer.

The strong correlation of the LDL Oxidative Response with triacylglycerols is important since elevated triacylglycerols are a prime component of metabolic syndrome which in turn has been shown to lead to cardiovascular disease. Elevated triacylglycerols through CETP activity produce small-dense LDL and low HDL and an increase in overall LDL particle numbers and Apo-B-100. Also important is that the oxidative response correlation with LDL cholesterol is much less than with triacylglycerols and this changes the emphasis for metabolic syndrome and cardiovascular disease from a cholesterol related disease more of a triacylglycerol related disease.

In the experiments that lead to the development of the LDL oxidative response, many variables of TG/VLDL Metabolism, TG/LDL Metabolism and HDL Metabolism assays were studied to produce the best measureable response. Due to the dynamic nature of these assays the reagents and their strength, incubation times and temperatures and the method of measurement all determine final result. Similar results in the underling lipoprotein properties can be obtained by changing these variables but the optimal conditions of the assays were obtained for the best magnitude of response, precision and accuracy.

The LDL oxidative response may not only be a function of the LDL's protection to oxidation but rather the entire body's protection to oxidation since antioxidants are protective throughout the body. LDL oxidation is just one response that is measurable in this regard. Additionally hypochlorous acid is only one of many oxidizing agents that can attack the human body and only one of many types of chemical oxidation that can affect LDL or other lipids and proteins in the body.

The body's resistance to chemical oxidation is a function of its natural anti-oxidant defenses, anti-oxidant foods and supplements and sources of oxidative stress. The end result of these oxidative and anti-oxidative components can result in atherosclerosis and many other forms of aging.

Incubation Assay—The control profile prepared using the same dilution and incubation conditions as in the oxidation experiment shows a number of distinct modifications relative to the standard LPP profile. The most obvious change is a shift of the LDL subgroups to a more buoyant or less dense position. The percent density change is significant and measurable and in many cases, especially where VLDL is elevated, is reflected by a movement of VLDL subgroups from a more buoyant to a less buoyant position. The exchange of lipids, usually triacylglycerols from VLDL to LDL and HDL and cholesterol ester from LDL and HDL to VLDL is well known, when triacylglycerols are elevated and is performed by CETP in vivo. A movement of triacylglycerols into LDL would lower the density of these particles and cause the observed density shift. The loss of triacylglycerols and increase in cholesterol ester for VLDL would increase the density of these particles and account for the observed density shift there as well. This indicator was named a "TG/LDL-CETP Activation" assay since it appears to be due to CETP activity and is highly correlated to triacylglycerol levels, small-dense LDL and Apo B-100 levels.

One might expect that the HDL density movement is due to the same process as observed in LDL particles and the result of CETP activity however there doesn't appear to be a strong correlation between the HDL density shift and the TG/LDL-CETP Avtivation indicator or a strong correlation with other lipid indicators of atherosclerosis such as small-dense LDL or Apo B-100. The easily measured HDL particle density movement into HDL2b is correlated to a clear reduction in HDL3, so when triacylglycerols are moderate it is believed to be the non-atherogenic process of reverse cholesterol transport. In this process un-esterified cholesterol, probably caught in the exchange of cholesterol from LDL to VLDL in CETP activity, is esterified by the enzyme LCAT and incorporated into HDL creating the more buoyant HDL2b. When triacylglycerols are elevated large movements of HDL to a more buoyant position are observed and this is believed to be a combination of triacylglycerol transfer to HDL and reverse cholesterol transport. This indicator was named "HDL-CETP/LCAT Activation" as a measure of both CETP and LCAT activity through reverse cholesterol transport. Additionally during the incubation process a reduction in the overall LDL particle numbers are observed, especially in healthy individuals, and this is believed to be from LDL attack from LCAT breaking up the particles and releasing the various lipids including, un-esterifed cholesterol which is esterifed by LCAT and cholesterol ester which are then incorporated into HDL generating HDL 2b. The decrease in LDL particle numbers is measure and called LDL-LCAT Activation.

Figure 1:
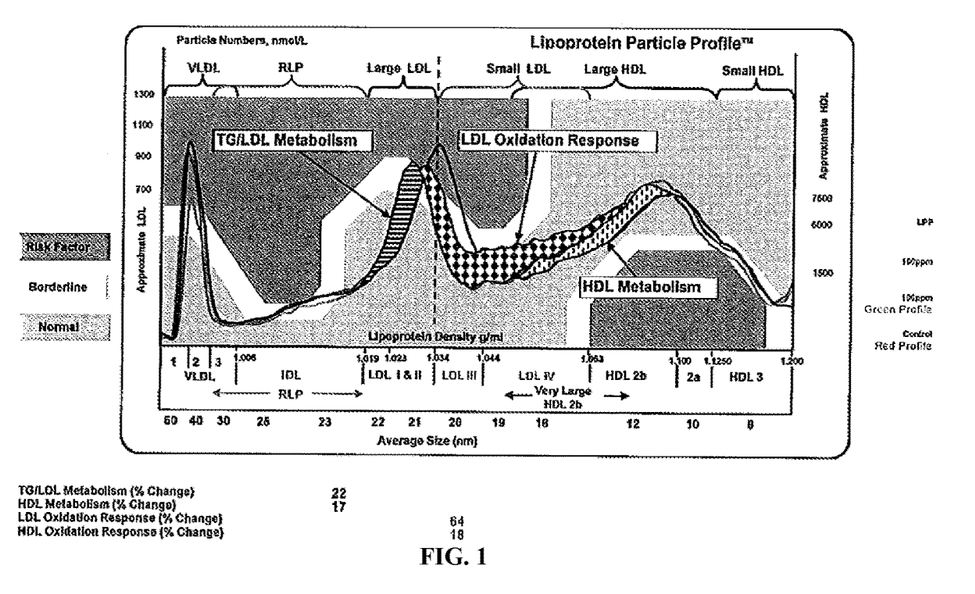
FIG. 1. Plot Showing LDL Oxidation Response, TG/LDL Metabolism and HDL Metabolism Assays.
Figure 2:
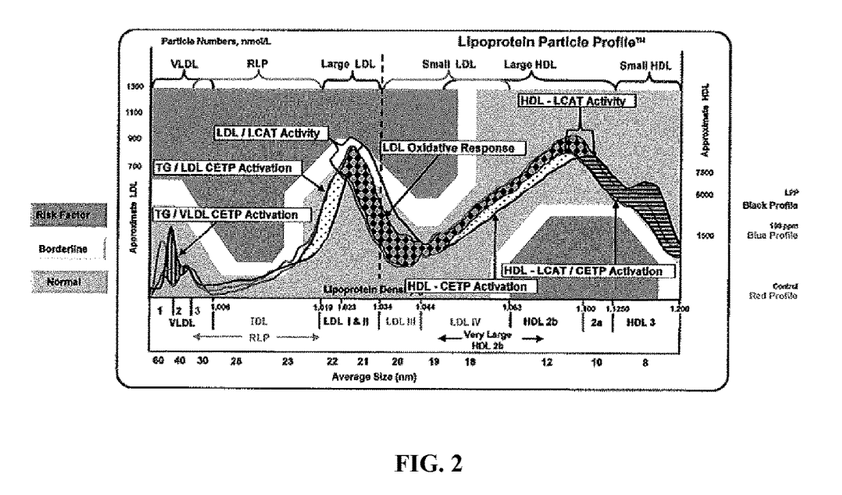
FIG. 2. Plot showing LDL Oxidative Response, HDL Oxidative response, TG/VLDL-CETP Activation, TG/LDL-CETP Activation, LDL-LCAT Activation, HDL-CETP/LCAT Activation and HDL-LCAT Activation Assays.

In the incubation assay to measure the HDL metabolism, it could be better to measure the reduction in HDL 2a and HDL 3 than the increase in HDL 2b since this increase is a measure of both CETP and LCAT activity. This assay is called HDL-LCAT Activation. HDL 2b seems to be highly correlated to triacylglycerol levels when high and not then necessarily correlated to HDL reverse cholesterol transport where LCAT metabolism would be involved. Attached is a new diagram of the profile labeling all of the potential assays. The reduction in HDL2a and HDL 3 appears to be more independent of triacylglycerol levels except that a total movement of the HDL peak due to triacylglycerols, making it more buoyant, can look like HDL 3 reduction. When triacylglycerols are low then it is clear that HDL 2a and HDL3 reduction must be reverse cholesterol transport aided by LCAT through the esterification of cholesterol from the LDL particles being transferred to HDL.

A reduction in both LDL particles and cholesterol in the chemistries was observed and shown as LDL/LCAT Activity, such as reduction in LDL I, LDL II and/or LDL III.

An increase in HDL particle numbers and in cholesterol chemistries was observed and shown as HDL-CETP/LCAT Activity.

It may be contemplated a large reduction in HDL 2a and HDL 3 is correlated to less healthy individuals, and an increase in HDL 2b, which may be called HDL-CETP/LCAT Activity, is correlated with a healthy profile. This value goes from an increase on incubation in total HDL particles for healthy people to a large decrease in HDL 2a and HDL particles for unhealthy people. This movement can be important and measured if triacylglycerols do not interfere heavily.

LCAT activity may be correlated with cardiovascular disease, even though reverse cholesterol transport is supposed to be a healthy process. The difference may be the difference between normal in vivo activity verses re-activation of LCAT through incubation.

When triacylglycerols are elevated we see a large movement in the incubated serum in LDL to a more buoyant position which we reported and call TG/LDL CETP Metabolism or Activation. This movement is also correlated to a reduction in especially the large triacylglycerol containing VLDL particles as would be expected from CETP activity. We also see a reduction in LDL cholesterol chemistries where the cholesterol is replaced by triacylglycerols and the cholesterol goes back to the VLDL particles making them more buoyant. Each of these may be reportable assays with varying levels of uniqueness and importance. The VLDL change we call TG/VLDL-CETP Activation. The particle number decrease in LDL called LDL-LCAT Activation may be due to a number of factors. It was already mentioned that it could be due to un-esterified cholesterol in LDL being chewed up by LCAT and transferred to HDL but other factors may be involved. A reduction in LDL particle numbers is sometimes associated with unhealthy people but more commonly associated healthy people and believed to be healthy LCAT activity.

In the incubation assay, which is a reagent less assay, the serum was incubated for 20 hours at 37 degrees C. This sample was the control for the LDL Oxidative Response assay. The percent change in LDL and HDL density relative to the standard LPP assay where the serum is not incubated was measured.

For LDL, a movement of LDL to a more buoyant position which seems to be correlated to triacylglycerol levels (extra TG's makes the LDL more buoyant) was observed, so it appears to be an accelerated version of the known process of lipid transfer by CETP where TG's are moved to LDL and cholesterol is moved back to VLDL. This transfer was also seen in chemistries and the result should be highly correlated to diabetic tendencies. This result is called "TG/LDL-CETP Metabolism."

The HDL movement appears to more complex and not simply the effect of accelerated reverse cholesterol transport or LCAT activity. The disappearance of smaller dense HDL and sometimes the formation of larger, more buoyant HDL were observed. So the assay is calculated from the disappearance of the small HDL 2a and 3 species relative to an un-incubated LPP profile. This assay was called "HDL-LCAT Avtivation" and high results seems to be related to a person's un-used HDL potential where LCAT esterifies cholesterol and converts HDL 3's to HDL 2b's. In our survey, when high, this is correlated to less healthy individuals however we don't totally understand what is in play in this assay.

The following table 1 summarizes the measurements and corresponding parameters in the incubation assay (the first five rows) and the oxidation assay (the last two rows).

TABLE 1

Incubation Assays and Oxidative Response Assays

| Analyte Control | Health-Indication | Lipoprotein Subgroups | Particles Numbers | Cholesterol |
|---|---|---|---|---|
| Incubation Assays with Possible Activation: | | | | |
| | | | | Un-incubated |
| 1. TG/VLDL-CETP LPP | Activation Reduced if down & TG's are elevated | VLDL-L, VLDL-S | VLDL-L↓↓ + VLDL-S↕ | VLDL↑ |
| 2. TG/LDL-CETP LPP | Activation Reduced if up | LDL I, LDL II | LDL I ↑↑ + LDL II↕ | LDL↓ |
| 3. LDL-LCAT LPP | Activation Improved if down | LDL I, LDL II, LDL III | LDL I + II + III ↓ | LDL↓ |

TABLE 1-continued

Incubation Assays and Oxidative Response Assays

| Analyte Control | Health-Indication | Lipoprotein Subgroups | Particles Numbers | Cholesterol |
|---|---|---|---|---|
| 4. HDL-CETP/LCAT LPP | Activation Reduced if up & TG's are elevated | HDL 2b | HDL 2b ↑↑ | HDL ↕ |
| 5. HDL-LCAT LPP | Activation Reduced if down | HDL 2a, HDL 3 | HDL 2a ↕ + HDL 3 ↓↓ | HDL ↕ |

Oxidation Assays:

| | | | Incubated | |
|---|---|---|---|---|
| 6. LDL LPP | Oxidative Response Reduced if up | LDL II, III, IV, HDL 2b | LDL II + III + IV + HDL 2b ↑ | |
| 7. HDL LPP | Oxidative Response Reduced if up | HDL 2a, HDL 3 | HDL 2a + 3 ↑ | |

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The invention claimed is:

1. A method for generating an oxidation susceptibility lipoprotein profile for a for a subject, comprising the steps of:
   (a) generating a base lipid particle profile by (i) separating a first portion of a test blood sample into very low density lipoprotein (VLDL), intermediate density lipoprotein (IDL), LDL I, LDL II, LDL III, LDL IV, high density lipoprotein (HDL) 2b, HDL 2a, and HDL 3 subgroups, (ii) measuring an amount or percentage or both of one or more of the subgroups or an amount of cholesterol in one or more subgroups;
   (b) generating an oxidized lipid particle profile by (i) oxidizing a second portion of the blood sample with an external oxidizing agent, (ii) separating the second portion of the test blood sample into VLDL, IDL, LDL I, LDL II, LDL III, LDL IV, HDL 2b, HDL 2a, and HDL 3 subgroups, (iii) measuring an amount or percentage or both of one or more of the subgroups or an amount of cholesterol in one or more subgroups;
   (c) comparing the base lipid particle profile with the oxidized lipid particle profile by comparing the measured amounts or percentage of corresponding one or more subgroups, or amounts of cholesterol in corresponding one or more subgroups to determine the oxidation susceptibility lipoprotein profile for the subject.

2. The method of claim 1, further comprising calculating the CETP or LCAT activity.

3. The method of claim 1, wherein the measuring step further comprises comparing the measurement to a control or reference.

4. The method of claim 1, wherein the test blood sample is a serum or plasma sample.

5. The method of claim 1, wherein the oxidizing agent is myeloperoxidase and $H_2O_2$; hypochlorite; or hypochlorous acid.

6. The method of claim 1, wherein the oxidizing agent is 1-300 ppm hypochlorite or hypochlorous acid.

7. The method of claim 1, wherein the oxidizing step comprises 1 minute to 48 hours incubation with the external oxidizing agent.

8. The method of claim 1, wherein the oxidizing step is performed at a temperature of 10 to 50° C.

9. The method of claim 1, wherein the separating steps comprise placing the first portion or the second portion of the test blood sample on a continuous gradient ranging in density from 1.000 g/ml to 1.300 g/ml.

10. The method of claim 1, wherein the separating steps comprise the use of ion mobility, electrophoresis, nuclear magnetic resonance (NMR) or analytical ultracentrifugation.

11. The method of claim 1, wherein the separating steps comprise the use of analytical ultracentrifugation.

12. The method of claim 1, wherein the separating steps comprise the use of analytical ultracentrifugation at about 120,000 rpm at 22° C. for 1 hour.

13. The method of claim 1, wherein the separating steps comprise adding a fluorescent agent to the test blood sample prior to or during separation.

14. The method of claim 13, wherein the fluorescent agent is an NBD fluorophore.

15. The method of claim 3, wherein the control is a blood sample incubated in a buffer or water for the same time and the same dilution ratio as step (a) and/or (b).

16. The method of claim 1, further comprising diagnosing the subject for the risk of developing cardiovascular diseases based on the lipoprotein profile.

17. The method of claim 16, further comprising treating the subject at risk of developing cardiovascular diseases.

18. The method of claim 17, wherein treating the subject comprises prescribing, administering or recommending antioxidants or reducing oxidants in the subject.

19. The method of claim 1, further comprises repeating steps (a) to (c) periodically to monitor the subject's lipoprotein profile.

* * * * *